(12) United States Patent
Grundschober et al.

(10) Patent No.: US 7,872,022 B2
(45) Date of Patent: Jan. 18, 2011

(54) SEROTONIN TRANSPORTER (SERT) INHIBITORS FOR THE TREATMENT OF DEPRESSION AND ANXIETY

(75) Inventors: Christophe Grundschober, Rodersdorf (CH); Patrick Schnider, Bottmingen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 970 days.

(21) Appl. No.: 11/726,931

(22) Filed: Mar. 23, 2007

(65) Prior Publication Data

US 2007/0232652 A1    Oct. 4, 2007

(30) Foreign Application Priority Data

Apr. 3, 2006    (EP) .................. 06112170

(51) Int. Cl.
  *A61K 31/445* (2006.01)
  *C07D 211/18* (2006.01)

(52) U.S. Cl. .................. 514/317; 514/331; 514/357; 546/229; 546/234; 546/330; 546/339

(58) Field of Classification Search .............. 514/331, 514/317, 357; 546/229, 234, 236, 330, 339
  See application file for complete search history.

(56) References Cited

U.S. PATENT DOCUMENTS

| 5,328,917 | A | 7/1994 | Jakobsen et al. |
| 6,136,824 | A | 10/2000 | Macleod et al. |
| 6,297,375 | B1 | 10/2001 | Bös et al. |

FOREIGN PATENT DOCUMENTS

| DE | 10008042 | 8/2000 |
| WO | WO 98/47514 | 10/1998 |
| WO | WO 01/29031 | 4/2001 |
| WO | WO 2003/015784 | 2/2003 |
| WO | WO 2005/032464 | 4/2005 |

OTHER PUBLICATIONS

Froger et al., J. Neuroscience, vol. 21 (20), pp. 8188-8197 (2001).
Kramer et al., Science, vol. 281, pp. 1640-1645 (1998).
Millan et al., J. Neurochem. vol. 76, pp. 1949-1954 (2001).
Rupniak, N., Can. J. Physiol. Pharmacol. vol. 80, pp. 489-494 (2002).
Rupniak, N., Current Opinion in Investigational Drugs, vol. 3(2), pp. 257-261 (2002).
Ryckmans et al., Bioorg. Med. Chem. Lett. vol. 12(2), pp. 261-264 (2002).
Ryckmans et al., Bioorg Med. Chem. Lett. vol. 12(21), pp. 3195-3198 (2002).

*Primary Examiner*—Celia Chang
(74) *Attorney, Agent, or Firm*—George W. Johnston; Patricia S. Rocha-Tramaloni; Kimberly J. Prior

(57) ABSTRACT

The present invention relates to trans-derivatives of formula

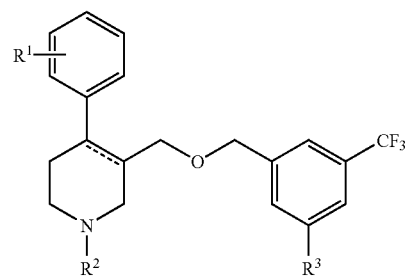

I wherein $R^1$, $R^2$, $R^3$, and the dotted line are as defined herein and to pharmaceutically acceptable acid addition salts thereof.

The compounds of formula I are good inhibitors of the serotonin transporter (SERT inhibitors) and simultaneously, they have good activity on the NK-1 receptor (dual effect). By virtue of their efficacy as SERT inhibitors, the compounds in the present invention are particularly useful for the treatment of CNS disorders and psychotic disorders, in particular in the treatment or prevention of depressive states and/or in the treatment of anxiety.

6 Claims, No Drawings

SEROTONIN TRANSPORTER (SERT) INHIBITORS FOR THE TREATMENT OF DEPRESSION AND ANXIETY

PRIORITY TO RELATED APPLICATIONS

This application claims the benefit of European Application No. 06112170.3, filed Apr. 3, 2006, which is hereby incorporated by reference in its entirety.

BACKGROUND OF THE INVENTION

SERT Inhibitors, including the selective serotonin transporter inhibitors, also called selective serotonin reuptake inhibitors (SSRI's), have become the most frequently prescribed antidepressant drugs. They are believed to exert their effect by increasing extracellular 5-HT levels in the serotoninergic terminal fields such as the hippocampus and prefrontal cortex. However, approximately 30% of patients appear to be resistant to SSRI treatment. In addition, those patients who do benefit from SSRI treatment often exhibit various side-effects which include sexual dysfunction, gastrointestinal distress, insomnia and in some cases anxiogenesis due to their indirect activation (through elevation of 5-HT levels) of all 5-HT receptors.

Furthermore, a common problem in current antidepressant therapies is their slow onset of action, since a delay of about 4 weeks is normally observed between the beginning of the treatment and alleviation of the symptoms. The delay appears to parallel the progressive desensitization of somatodendritic $5HT_{1A}$ receptors, increasing serotoninergic function, thus allowing alleviation of depressive symptoms.

Recent reports have indicated that the combination of a SSRI and a NK-1 antagonist produces beneficial responses in animal models of anxiety and depression such as guinea-pig pup maternal separation vocalization, with relatively reduced doses (WO98/47514;. *Bioorg. Med. Chem. Lett.* 12(2), 261-264 (2002) and *Bioorg. Med. Chem. Lett.* 12(21), 3195-3198 (2002).

This suggests that by adopting a dual approach which is mechanistically dissimilar, a synergism between the two modes of action may occur, enabling enhanced responses. This may not only be beneficial in patients resistant to treatment with SSRI alone but also in improving the rapidity of onset of therapeutic action. A drug with a dual mode of action potentially allows for a reduction in dosing and therefore a decreased risk of side effects as compared to a combination of two drugs.

In the patent literature the combined NK-1I/SSRI approach has also been proposed as a potential treatment for obesity (WO98/47514). WO2005/032464 describes trans-phenyl pyrrolidine ethers, which are tachykinin receptor antagonists.

REFERENCES

Froger, N., Gardier, A. M., Moratalla, R., et al., 5-HT1A autoreceptor adaptive changes in substance P (Neurokinin 1) receptor knock-out mice mimic antidepressant-induced desensitization. J. Neuroscience, 21(20), 8188-8197 (2001).

Kramer M. S., Cutler, N., Feighner, J. et al., Distinct Mechanism of antidepressant activity by blockade of central substance P receptors. Science 281, 1640-1645 (1998).

Millan, M. J., Lejeune, F., de Nanteuil, G. and Gobert, A., A selective blockade of neurokinin NK1 receptors facilitates the activity of adrenergic pathways projecting to the frontal cortex and dorsal hippocampus in rats. J. Neurochem., 76, 1949-1954 (2001).

Rupniak, N. M. J. New Insights into the antidepressant actions of substance P (NK1 receptor) antagonists. N. M. J Can. J. Physiol. Pharmacol. 80, 489-494 (2002).

Rupniak, N. M. J. Elucidating the antidepressant actions of substance P (NK1 receptor) antagonists. Current Opinion in Investigational Drugs, 3(2), 257-261 (2002).

Ryckmans, T., Balancon, L., Berton, O., et al., First dual NK1 antagonists-serotonin reuptake inhibitors: synthesis and SAR of a new class of potential antidepressants. Bioorg. Med. Chem. Lett. 12(2), 261-264 (2002).

Ryckmans, T., Berton, O., Grimee, R., et al., Dual NK1 Antagonists-serotonin reuptake inhibitors as potential antidepressants. Part 2 :SAR and activity of benzyloxyphenethyl piperazine derivatives. Bioorg. Med. Chem. Lett. 12(21), 3195-3198 (2002).

WO98/47514 A1. Use of an NK1 receptor antagonist and an SSRI for treating obesity.

WO03/015784 A1. 2-Substituted 1-arylpiperazines as tachykinin antagonists and/or serotonin reuptake inhibitors.

SUMMARY OF THE INVENTION

The present invention provides trans-derivatives of formula I

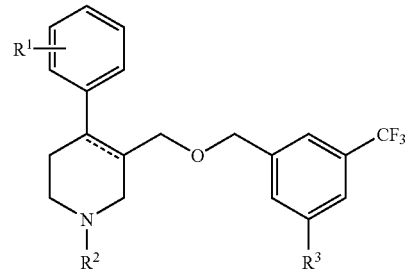

wherein $R^1$ is hydrogen, halogen or lower alkyl;

$R^2$ is hydrogen, lower alkyl or —$(CH_2)_n$CN;

$R^3$ is hydrogen or $CF_3$;

n is 1 or 2; and the dotted line represents an optional bond;

and pharmaceutically acceptable acid addition salts thereof.

Further encompassed by the present formula I are compounds of formulas

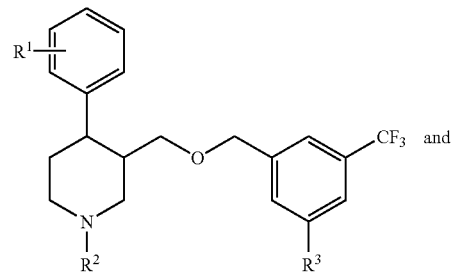

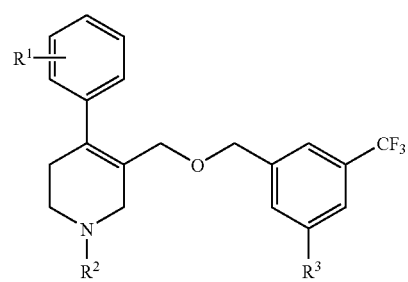

The invention includes all trans-derivatives and their pharmaceutically active salts.

The invention also provides a pharmaceutical composition containing one or more compound of formula I or a pharmaceutically acceptable salt thereof and a pharmaceutically acceptable carrier. The invention further provides methods for preparation of the compounds and compositions of the invention.

A small group of trans-derivatives of piperidine or tetrahydropyridine derivatives, i.e. those of formula I are good inhibitors of the serotonin transporter (SERT inhibitors) and simultaneously have good activity as NK-1 receptor antagonists (dual effect). A drug with a dual mode of action combines the advantages of both receptor sites, and the dosage of the drug can therefore be reduced, thus leading to a decreased risk of side effects as compared to a combination of two drugs.

By virtue of their efficacy as SERT inhibitors, the compounds in the present invention are particularly useful for the treatment of CNS disorders and psychotic disorders, in particular in the treatment or prevention of depressive states and/or in the treatment of anxiety.

Thus, combination of serotonin uptake inhibition with NK-1 antagonism may lead to compounds with an improved onset of action and a better efficacy during the treatment of depressive/anxiolytic states. Therefore, compounds of formula I have SERT inhibitory activity with an additional beneficial effect on the onset of action, which may allow major improvements for SSRI-resistant patients, e.g. with a reduced anxiogenic or even anxiolytic profile.

Compounds of formula I have good activity as SERT inhibitors and are concomitantly active as NK-1 receptor antagonists. NK-1 antagonists are believed to indirectly modulate 5-HT function via noradrenergic pathways and have been shown to attenuate presynaptic $5HT_{1A}$ receptor function (*Bioorg. Med. Chem., Lett.* 12, (2002), 261-264).

The compounds of the present invention combine serotonin transporter inhibition and NK-1 antagonism.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a saturated straight- or branched-chain hydrocarbon group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

The term "halogen" denotes chlorine, iodine, fluorine and bromine.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

The present invention provides trans-derivatives of formula I

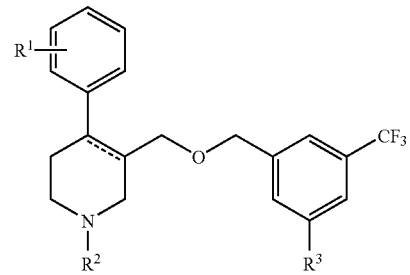

wherein
R¹ is hydrogen, halogen or lower alkyl;
R² is hydrogen, lower alkyl or —(CH₂)ₙCN;
R³ is hydrogen or CF₃;
n is 1 or 2; and
the dotted line represents an optional bond;
and pharmaceutically acceptable acid addition salts thereof.

Encompassed by the present formula I are compounds of formulas

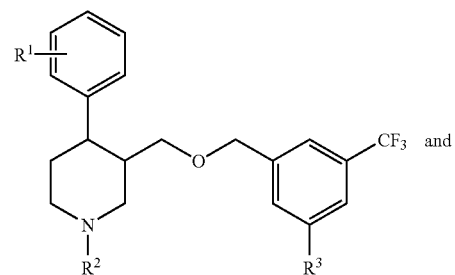

and

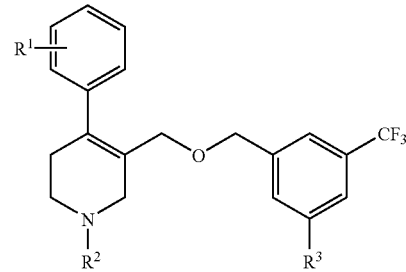

The invention includes all trans-derivatives and their pharmaceutically active salts.

Preferred compounds of formula I are those of formula IA, for example the following compounds:
(−)-(3S,4R)-3-(3,5-bis-trifluoromethyl-benzyloxymethyl)-4-(4-fluoro-phenyl)-piperidine,
(−)-(3S,4R)-3-(3,5-bis-trifluoromethyl-benzyloxymethyl)-4-(4-fluoro-phenyl) -piperidine, —(−)-[(3S,4R)-3-(3,5-bis-trifluoromethyl-benzyloxymethyl)-4-(4-fluoro-phenyl)-piperidin-1-yl]-acetonitrile,
(−)-(3S,4R)-4-(4-fluoro-phenyl)-3-(3-trifluoromethyl-benzyloxymethyl)-piperidine,
(3SR,4RS)-3-(3,5-bis-trifluoromethyl-benzyloxymethyl)-4-phenyl-piperidine and
(−)-(trans)-3-(3,5-bis-trifluoromethyl-benzyloxymethyl)-4-o-tolyl-piperidine.

Preferred compounds of formula I are further those of formula I-B, for example the following compound 5-(3,5-bis-trifluoromethyl-benzyloxymethyl)-4-o-tolyl-1,2,3,6-tetrahydro-pyridine.

The trans-derivatives of formula I (piperidine or tetrahydropyridine) have a dual activity and therefore they can share the advantages as mentioned above. In the table below are shown NK-1 and SERT activities of compounds of present trans-derivatives of formula I, as compared to structurally-related trans-derivatives of formulas II and III, not encompassed by the present invention.

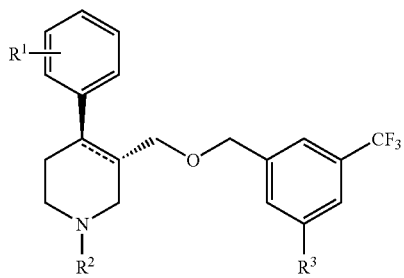

I

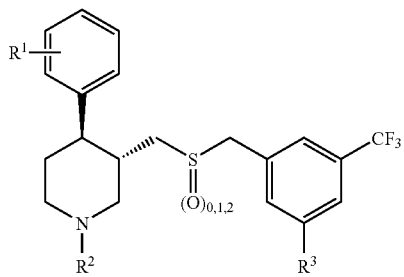

II

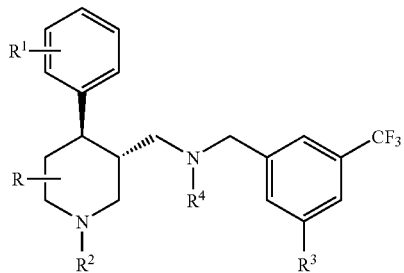

III

| Structure | pKi hSERT | pKi hNK1 | Example |
|---|---|---|---|
| (structure shown) | 8.21 | 7.9 | 1 of I present invention |

| | | | |
|---|---|---|---|
| [structure: 4-(4-fluorophenyl)-1-methyl-3-((3,5-bis(trifluoromethyl)benzyloxy)methyl)piperidine] | 6.97 | 8.09 | 2 of I present invention |
| [structure: 4-(4-fluorophenyl)-1-cyano-3-((3,5-bis(trifluoromethyl)benzyloxy)methyl)piperidine] | 6.85 | 7.67 | 3 of I present invention |
| [structure: 4-(4-fluorophenyl)-3-((3-(trifluoromethyl)benzyloxy)methyl)piperidine] | 7.77 | 6.83 | 4 of I present invention |
| [structure: 4-phenyl-3-((3,5-bis(trifluoromethyl)benzyloxy)methyl)piperidine] | 7.96 | 8.05 | 5 of I present invention |
| [structure: 4-(2-methylphenyl)-3-((3,5-bis(trifluoromethyl)benzyloxy)methyl)piperidine] | 7.49 | 7.62 | 6 of I present invention |

| | | | |
|---|---|---|---|
| 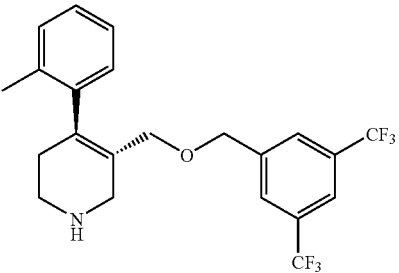 | 7.49 | 8.5 | 7 of I present invention |
| 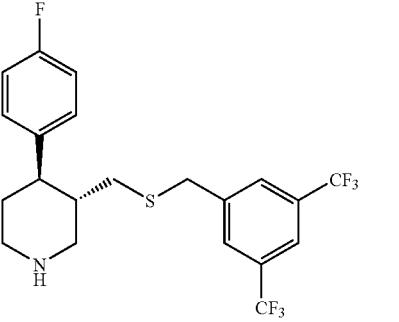 | 6.75 | 8.00 | 1 of II comparative data |
| 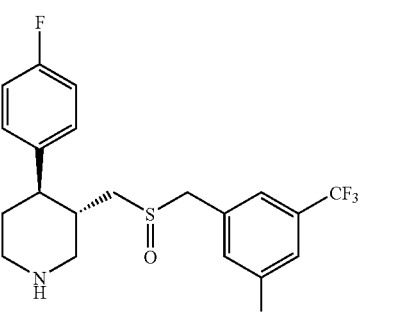 | 5.52 | 7.20 | 2 of II comparative data |
| 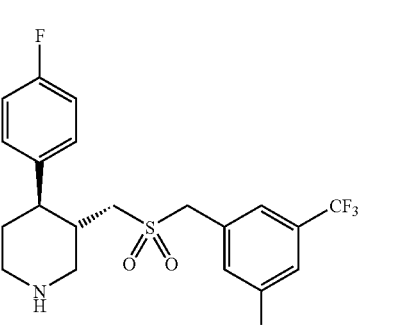 | | 7.87 | 3 of II comparative data |
|  | 6.14 | 7.90 | 1 of III comparative data |

| Structure | | | |
|---|---|---|---|
| (4-F-phenyl piperidine with CH2-N(CH3)-CH2-3,5-bis(CF3)phenyl) | 6.15 | 7.69 | 2 of III comparative data |
| (4-F-phenyl piperidine with CH2-N(COCH3)-CH2-3,5-bis(CF3)phenyl) | 5.00 | 7.86 | 3 of III comparative data |
| (4-F-phenyl piperidine with CH2-N(SO2CH3)-CH2-3,5-bis(CF3)phenyl) | 5.00 | 7.52 | 4 of III comparative data |

Related compounds of formulas II and III have a high selectivity to the NK-1 receptor (not desired in the present case).

The data has been generated in accordance with the following assays:

hSERT SPA Binding Assay

HEK-293 cells stably expressing recombinant human SERT are maintained with DMEM high glucose with 10% FBS, 300 μg/ml G418 and 2 mM L-Glutamine and incubated at 37° C. with 5% $CO_2$. Cells are released from culture flasks using PBS for 1-2 min. The cells are subsequently centrifuged at 1000 g's for 5 min and resuspended in PBS prior to being used in the membrane preparation.

Cells are homogenized using a Polytron in 50 mM Tris (pH 7.4). Centrifuged at 48,000×g for 15 min, and the pellet resuspended in fresh buffer. After a second centrifugation, the pellet is re-homogenized and resuspended in fresh buffer. Typically, membrane portions are aliquoted in 3 mg/ml (w:v). and stored at 80° C.

A serial dilution of test compounds in 50 mM Tris-HCl, 120 mM NaCl, KCl 5 mM (pH 7.4) is made in a white Optiplate (Packard) (100 μl/well) and the radioligand $^3[H]$ Citalopram (Specific activity: 60-86 Ci/mmol, Final concentration: 1 nM) is added at 50 μl/well. Membrane and beads are prepared to a ratio of 5 μg:0.6 mg, with 0.6 mg PVT-WGA Amersham beads (Cat# RPQ0282V) added per well. 50 μl of the membrane/bead mixture is added to the assay plate for a final volume of 200 μl. The mixtures are allowed to stand at room temperature for one hour, and are then counted on a Packard TopCount.

The % inhibition is calculated for each compound tested (with 100% binding being the value obtained with the incubation of membrane/beads and radioligand in buffer without compound minus the non-specific binding measured in presence of 10 μM Fluoxetine). The concentration producing 50% inhibition ($IC_{50}$) is determined using an iterative non-linear curve fitting technique. The inhibition dissociation constant (Ki) of each compound is determined according to the method of Cheng-Prusoff.

hNK-1 Binding Assay

The affinity of test compounds for the NK-1 receptor was evaluated at human NK-1 receptors in CHO cells transfected with the human NK-1 receptor using the Semliki virus expression system and radiolabelled with [³H]substance P (final concentration 0.6 nM). Binding assays were performed in HEPES buffer (50 mM, pH 7.4) containing BSA (0.04%) leupeptin (8 μg/ml), MnCl₂ (3 mM) and phosphoramidon (2 μM). Binding assays consisted of 250 μl of membrane suspension (1.25×10⁵ cells/assay tube), 125 μl of buffer of displacing agent and 125 μl of [³H] substance P. Displacement curves were determined with at least ten concentrations of the compound. The assay tubes were incubated for 60 min at room temperature after which time the tube contents were rapidly filtered under vacuum through GF/C filters presoaked for 60 min with PEI (0.3%) with 2×2 ml washes of HEPES buffer (50 mM, pH 7.4). The radioactivity retained on the filters was measured by scintillation counting. All assays were performed in duplicate in at least 2 separate experiments.

The inhibition dissociation constant (Ki) of each compound for NK1 is determined as described above for hSERT.

The present invention also provides pharmaceutical compositions containing compounds of the invention, for example compounds of formula I and their pharmaceutically acceptable acid addition salts, and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides a method for preparing compositions of the invention which comprises bringing one or more compounds of formula I and/or pharmaceutically acceptable acid addition salts thereof and, if desired, one or more other therapeutically valuable substances into a galenical administration form together with one or more therapeutically inert carriers.

Compounds of formula I are good inhibitors of the serotonin transporter (SERT inhibitors) and simultaneously have good activity as NK-1 receptor antagonists. These compounds are particularly useful for the treatment of CNS disorders and psychotic disorders, in particular in the treatment or prevention of depressive states and/or in the treatment of anxiety. The invention provides a method for the treatment of depression which comprises administering to an individual a therapeutically effective amount of a compound of formula I or a pharmaceutically acceptable salt thereof. The invention further provides a method for treating anxiety which comprises administering to an individual a therapeutically effective amount of a compound of formula I or a pharmaceutically acceptable salt thereof.

The compounds and compositions of the invention can be administered in a conventional manner, for example, orally, rectally, or parenterally. The compounds of the invention can be administered orally, for example, in the form of tablets, coated tablets, dragées, hard and soft gelatin capsules, solutions, emulsions, or suspensions. The compounds of the invention can be administered rectally, for example, in the form of suppositories or parenterally, for example, in the form of injectable solutions.

The dosage at which the compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or IA or of the corresponding amount of a pharmaceutically acceptable salt thereof. The daily dosage can be administered as single dose or in divided doses and, in addition, the upper limit can also be exceeded when this is found to be indicated.

The novel trans-derivatives of formula I and their pharmaceutically acceptable salts can be prepared by methods known in the art, for example by processes described below, which processes comprise a) reacting a compound of formula

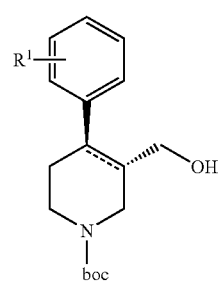

II with sodium hydride and a compound of formula

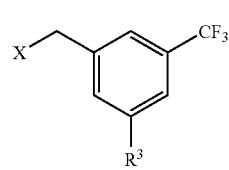

III followed by treatment with acid, such as HCl or trifluoroacetic acid, to give a compound of formula

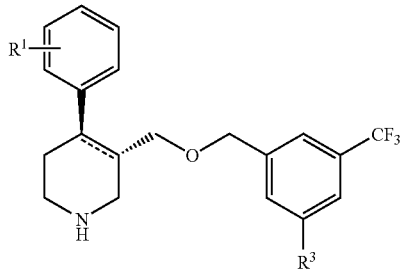

I-1 wherein X is Cl, Br or I and R¹ and R³ are as described above, or b) reacting a compound of formula

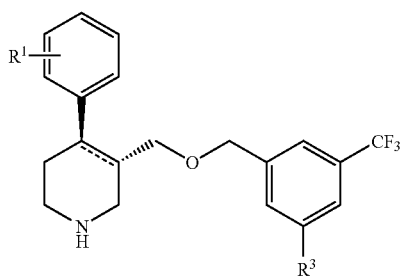

I-1 with a compound of formula

R²'CHO to give a compound of formula

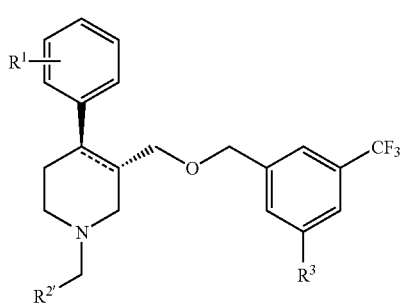

I-2 wherein R²' is $(CH_2)_n CN$ for n=1 or 2, or lower alkyl, with the exception of methyl and the other substituents are as described above, or c) reacting a compound of formula

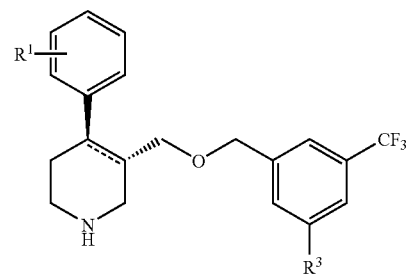

I-1 with a compound of formula R²X, wherein X is halide to give a compound of formula

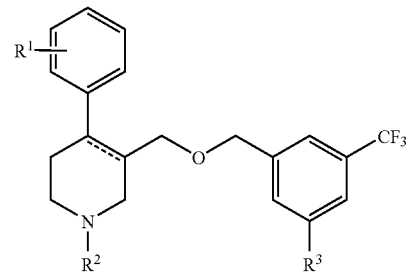

I or d) deprotecting a compound of formula

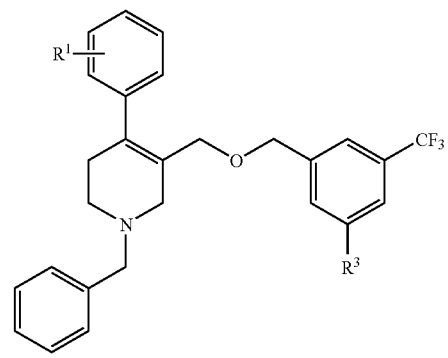

VII to give a compound of formula

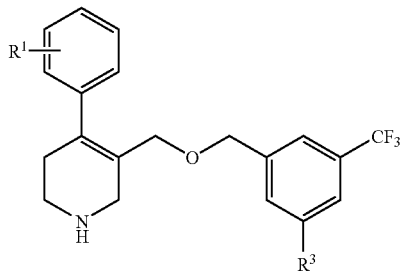

I-B' wherein R¹ is as described above, and, if desired, converting the compounds obtained into pharmaceutically acceptable acid addition salts.

Schemes 1 to 4 show the preparation of compounds of formula I in more detail. The starting material used in schemes 1 to 4 are known compounds or may be prepared by methods known in the art.

Scheme 1

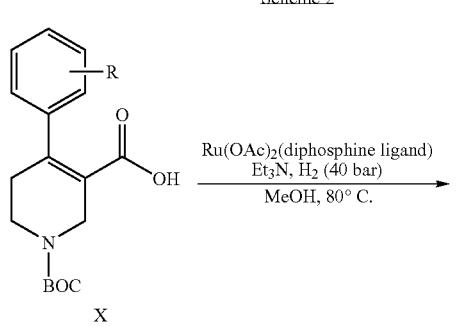

Scheme 2

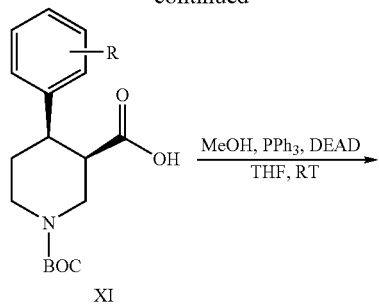

-continued

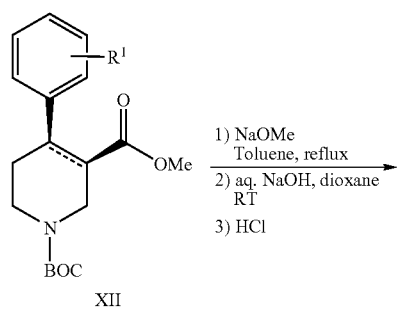

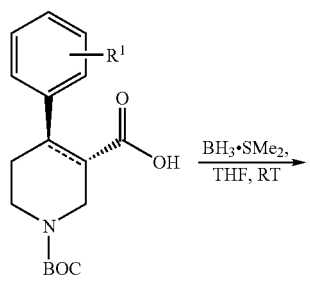

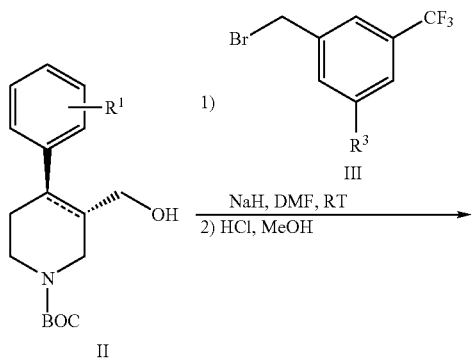

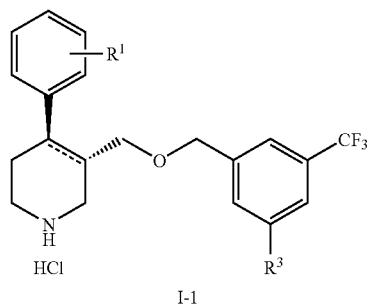

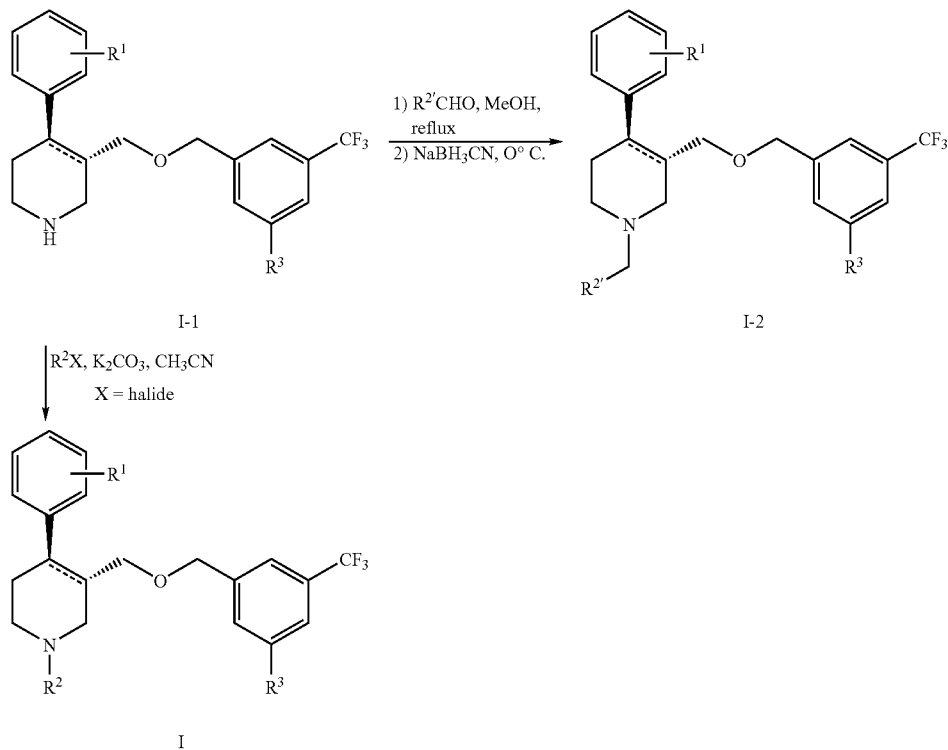
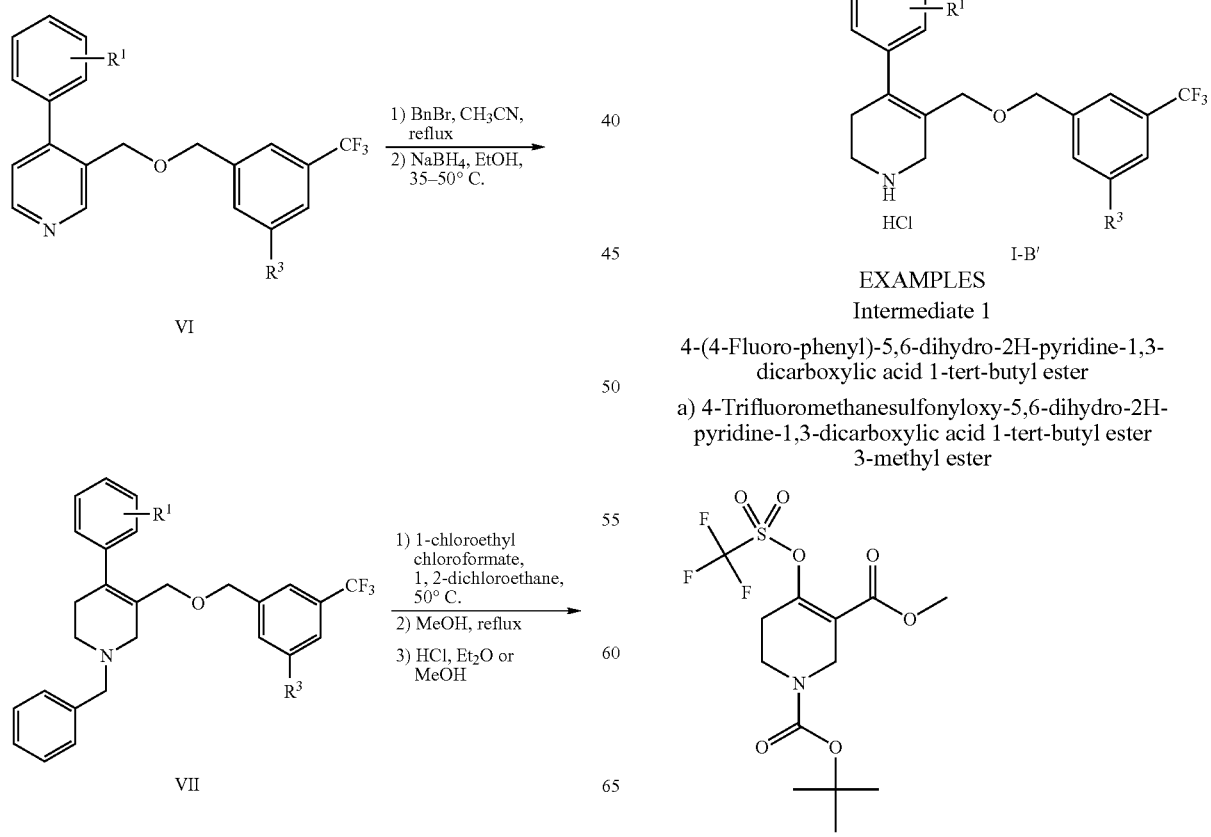
EXAMPLES
Intermediate 1
4-(4-Fluoro-phenyl)-5,6-dihydro-2H-pyridine-1,3-dicarboxylic acid 1-tert-butyl ester
a) 4-Trifluoromethanesulfonyloxy-5,6-dihydro-2H-pyridine-1,3-dicarboxylic acid 1-tert-butyl ester 3-methyl ester To a solution of 4-oxo-piperidine-1,3-dicarboxylic acid 1-tert-butyl ester 3-methyl ester (8.64 g, 33.5 mmol) in 230 ml THF was added sodium hydride (suspension in oil, 55%, 3.26 g, 74.6 mmol) at 0° C. After stirring for 30 min. at 0° C. N-phenyltrifluoromethanesulfonimide (20.4 g, 56.0 mmol) was added. The ice-water bath was removed and the reaction mixture was stirred for 2 days. Quenching with ice was followed by concentration in vacuo to remove THF. The residue was diluted with tert-butyl methyl ether and washed with three portions of 1 M aqueous sodium hydroxide solution. The organic layer was washed with brine and dried over sodium sulfate. Concentration in vacuo gave the crude title compound with a purity of 90% (11.4 g, 26.4 mmol, 71%).

MS m/e (%): 334 (M+H$^+$—C$_4$H$_8$, 100).

b) 4-(4-Fluoro-phenyl)-5,6-dihydro-2H-pyridine-1,3-dicarboxylic acid 1-tert-butyl ester 3-methyl ester

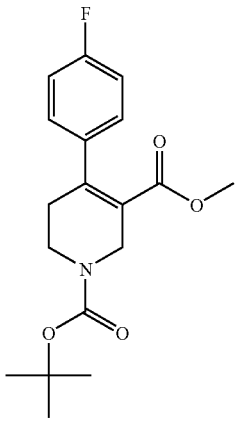

To a mixture of 4-trifluoromethanesulfonyloxy-5,6-dihydro-2H-pyridine-1,3-dicarboxylic acid 1-tert-butyl ester 3-methyl ester (10.1 g, 25.9 mmol), 4-fluorophenylzinc bromide solution (0.5 M in THF, 86.3 ml, 43.1 mmol) and 290 ml THF was added tetrakis(triphenylphosphine)palladium(0) (0.83 g, 0.72 mmol) at RT. After stirring for 6 h the reaction was quenched with ice. The mixture was diluted with tert-butyl methyl ether and washed with 2 M aqueous sodium carbonate solution. The aqueous layer was extracted with two portions of tert-butyl methyl ether. The combined organic layers were washed with brine, dried over sodium sulfate and concentrated in vacuo. Purification of the residue by flash chromatography (heptane/ethyl) gave the title compound as a lightly yellow amorphous residue (6.8 g, 71%).

MS m/e (%): 336 (M+H$^+$, 10).

c) 4-(4-Fluoro-phenyl)-5,6-dihydro-2H-pyridine-1,3-dicarboxylic acid 1-tert-butyl ester

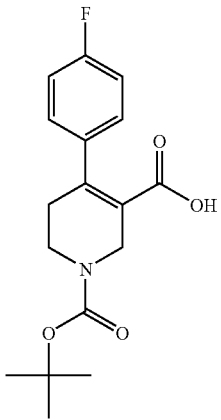

A mixture of 4-(4-fluoro-phenyl)-5,6-dihydro-2H-pyridine-1,3-dicarboxylic acid 1-tert-butyl ester 3-methyl ester (6.8 g, 20 mmol), 100 ml 1,4-dioxane and 100 ml 2 M NaOH was stirred at RT for 20 h. After extraction of the reaction mixture with two portions of tert-butyl methyl ether, the combined organic layers were extracted with 1 M aqueous sodium hydroxide solution (100 ml). The combined aqueous layers were cooled to 0° C. by addition of ice (150 g) and acidified to pH 1 with ice-cold 4 M aqueous hydrochloric acid solution (70 ml). The aqueous layer was extracted with three 150 ml-portions of ethyl acetate. The combined organic layers were washed with brine (50 ml), dried over sodium sulfate and concentrated in vacuo. Crystallization of the crude acid (6.4 g) from a mixture of n-heptane and ethyl acetate (19:1, 120 ml) gave the title compound as white crystals (5.1 g, 78%).

MS m/e (%): 320 (M−H$^+$, 100).

Intermediate 2

4-Phenyl-5,6-dihydro-2H-pyridine-1,3-dicarboxylic acid 1-tert-butyl ester

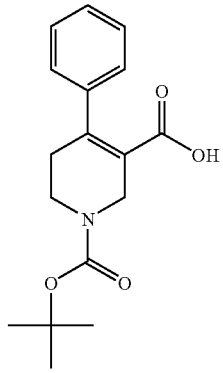

The title compound was obtained as white crystals in comparable yields according to the procedures described above for the preparation of 4-(4-fluoro-phenyl)-5,6-dihydro-2H-pyridine-1,3-dicarboxylic acid 1-tert-butyl ester using phenylzinc iodide instead of 4-fluorophenylzinc bromide in step b).

MS m/e (%): 302 (M−H$^+$, 100)

Intermediate 3

4-o-Tolyl-5,6-dihydro-2H-pyridine-1,3-dicarboxylic acid 1-tert-butyl ester a) 4-o-Tolyl-5,6-dihydro-2H-pyridine-1,3-dicarboxylic acid 1-tert-butyl ester 3-methyl ester

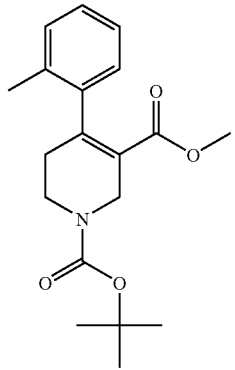

To a 1 M solution of o-tolylmagnesium chloride in THF (6.26 ml, 41.5 mmol) was added dropwise a freshly prepared solution of dried zink chloride (8.48 g, 62.2 mmol) in dry THF (200 ml) at 0° C. After completed addition the reaction mixture was allowed to slowly warm to room temperature over a period of 1 h. To this mixture were added a solution of 4-trifluoro-methanesulfonyloxy-5,6-dihydro-2H-pyridine-1,3-dicarboxylic acid 1-tert-butyl ester 3-methyl ester (10.7 g, 27.5 mmol) in THF (270 ml) and tetrakis(triphenylphosphine)palladium(0) (0.96 g, 0.83 mmol). After stirring for 6 h at room temperature the reaction was quenched with ice. The mixture was diluted with tert-butyl methyl ether and washed with 2 M aqueous sodium carbonate solution. The aqueous layer was extracted with two portions of tert-butyl methyl ether.

The combined organic layers were washed with water and brine, dried over sodium sulfate and concentrated in vacuo. Purification of the residue by flash chromatography (heptane/ethyl acetate) gave the title compound as a light yellow viscous oil (6.31 g, 69%).

MS me (%): 332 (M+H$^+$, 16).

b) 4-o-Tolyl-5,6-dihydro-2H-pyridine-1,3-dicarboxylic acid 1-tert-butyl ester

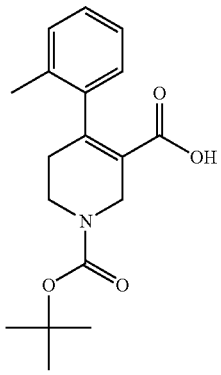

The title compound was obtained as white crystals after crystallization from n-heptane/ethyl acetate 19:1 in comparable yield according to the procedure described above for the preparation of 4-(4-fluoro-phenyl)-5,6-dihydro-2H-pyridine-1,3-dicarboxylic acid 1-tert-butyl ester using 4-o-tolyl-5,6-dihydro-2H-pyridine-1,3-dicarboxylic acid 1-tert-butyl ester 3-methyl ester instead of 4-(4-fluoro-phenyl)-5,6-dihydro-2H-pyridine-1,3-dicarboxylic acid 1-tert-butyl ester 3-methyl ester in step c).

MS m/e (%): 316 (M−H$^+$, 100)

Example 1

(−)-(3S,4R)-3-(3,5-Bis-trifluoromethyl-benzyloxymethyl)-4-(4-fluoro-phenyl)-piperidine hydrochloride a) (+)-(3R,4R)-4-(4-Fluoro-phenyl)-piperidine-1,3-dicarboxylic acid-1-tert-butyl ester

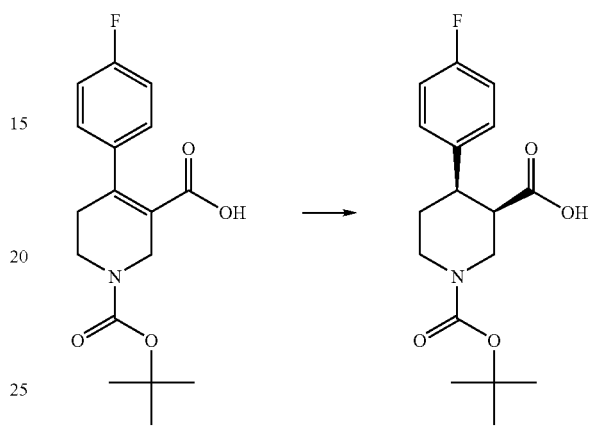

In a glove box (O$_2$ content ≦2 ppm) a 35 ml autoclave equipped with a 15 ml glass insert and a magnetic stirring bar was charged with 4-(4-fluoro-phenyl)-5,6-dihydro-2H-pyridine-1,3-dicarboxylic acid-1-tert-butyl ester (0.300 g, 0.934 mmol), [Ru(OAc)$_2$((S)-3,5-Xyl-4-MeO)-MeOBIPHEP] (9.67 mg, 0.00936 mmol), triethylamine (15 mg, 0.16 mmol, 0.16 eq.) and 5 ml of methanol. The asymmetric hydrogenation was run for 42 h at 80° C. under 40 bar of hydrogen. After cooling to room temperature the pressure was released from the autoclave, the methanol solution was diluted with 50 ml of tert-butyl methyl ether and extracted with two 50-ml portions of a 1 M aqueous sodium hydroxide solution. The aqueous layer was poured on ice, acidified with ice-cold 2 M aqueous hydrochloric acid solution to pH 1 and extracted with two 100-ml portions of ethyl acetate. The combined organic layers were dried over sodium sulfate, filtered and concentrated in vacuo to give (+)-(3R,4R)-4-(4-fluoro-phenyl)-piperidine-1,3-dicarboxylic acid-1-tert-butyl ester in 89% yield (0.27 g) and with 96.6% ee.

MS m/e (%): 322 (M−H$^+$, 100).

GC Method for ee Determination:

A 2-mg sample of the title compound was converted to the methyl ester by treatment with 0.5 ml of an approximately 0.5 M solution of diazomethane in diethyl ether at room temperature. After evaporation of excess diazomethane and diethyl ether under a gentle stream of argon the residue was dissolved in 1 ml of ethyl acetate. BGB-175 column, 10 m*0.1 mm*df 0.1 μm, hydrogen 230 kPa, split ratio 1:300; temperature gradient 100-200° C., program with 2° C./min; injector temperature 200° C., detector temperature 210° C. Retention times: 46.59 min (methyl ester of (+)-acid), 46.76 min (methyl ester of (−)-acid).

b) (+)-(3R,4R)-4-(4-Fluoro-phenyl)-piperidine-1,3-dicarboxylic acid 1-tert-butyl ester 3-methyl ester

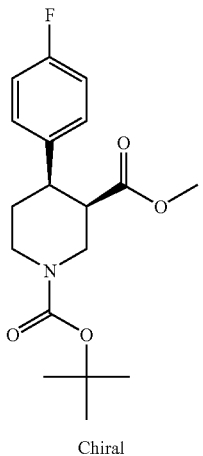

Chiral

To a solution of triphenylphosphine (3.82 g, 14.6 mmol) in 70 ml tetrahydrofuran was added diethyl azodicarboxylate (2.53 g, 14.6 mmol) at 0° C. After 30' methanol (4.55 ml, 112.0 mmol) and a solution of (+)-(3R,4R)-4-(4-fluoro-phenyl)-piperidine-1,3-dicarboxylic acid 1-tert-butyl ester (3.62 g, 11.2 mmol, 93.6% ee) in 30 ml tetrahydrofuran were added subsequently at 0-5° C. The reaction mixture was stirred for 20 h at room temperature. Quenching with water was followed by extraction with tert-butyl methyl ether (3×100 ml). The combined organic layers were dried over sodium sulfate, concentrated under reduced pressure and purified by flash chromatography (n-heptane/ethyl acetate) to give the title compound (3.55 g, 94%) as a colorless oil.

MS m/e (%): 338 (M+H$^+$, 28).
[α]$_D$=+68.69 (c=0.310, CHCl$_3$)
[α]$_{578}$=+71.27 (c=0.310, CHCl$_3$)
[α]$_{365}$=+221.60 (c=0.310, CHCl$_3$)

c) (−)-(3S,4R)-4-(4-Fluoro-phenyl)-piperidine-1,3-dicarboxylic acid 1-tert-butyl ester

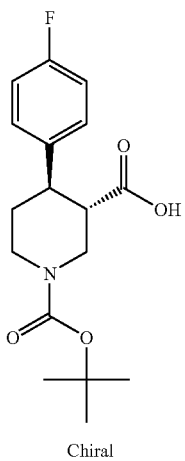

Chiral

A mixture of (+)-(3R,4R)-4-(4-fluoro-phenyl)-piperidine-1,3-dicarboxylic acid 1-tert butyl ester 3-methyl ester (3.55 g, 10.5 mmol) and sodium methoxide (1.14 g, 21.1 mmol) in 100 ml anhydrous toluene was heated at reflux over night. After cooling to room temperature the reaction mixture was quenched with water and concentrated in vacuo. The residue was dissolved in a mixture of 100 ml 1,4-dioxane and 50 ml 2 M aqueous sodium hydroxide solution. After stirring at RT for 5 h the mixture was diluted with water and washed with two portions of tert-butyl methyl ether. The aqueous layer was cooled to 0° C., acidified to pH 1-2 with ice-cold 1 M aqueous hydrochloric acid solution and extracted with three portions of tert-butyl methyl ether. The combined organic layers were dried over sodium sulfate and concentrated in vacuo. Flash column chromatography and crystallization from heptane/ethyl acetate 9:1 (30 ml) gave the title compound as white crystals (1.76 g, 52%, 97.5% ee).

MS m/e (%): 322 (M−H$^+$, 100).
[α]$_D$=−0.650 (c=0.154, CHCl$_3$)

HPLC Method for ee Determination:
Chiralpak-OD-H column, 25 cm*4.6 mm, 95% n-heptane+5% 2-propanol with 0.1% trifluroacetic acid, flow 0.7 ml/min, 30° C., 0.001 ml injection volume, 210 nm. Retention times: (−)-acid 9.5 min, (+)-acid 11.5 min.

Assignment of the Absolute Configuration

The absolute configuration of the title compound was assigned as (3S,4R) by comparison of the optical rotation and the retention time by HPLC analysis on a Chiralpak-OD-H column with the values of a sample of (−)-(3S,4R)-4-(4-fluoro-phenyl)-piperidine-1,3-dicarboxylic acid 1-tert-butyl ester which was derived from (−)-(3S,4R)-4-(4-fluoro-phenyl)-1-methyl-piperidine-3-carboxylic acid methyl ester (prepared as described in WO0129031) as follows:

A solution of (−)-(3S,4R)-4-(4-fluoro-phenyl)-1-methyl-piperidine-3-carboxylic acid methyl ester (575 mg, 2.29 mmol) and 1-chloroethyl chloroformate (393 mg, 2.75 mmol) in 5 ml 1,2-dichloroethane was heated at reflux for 4 h. After cooling to room temperature and evaporation of the solvent in vacuo the residue was dissolved in 5 ml methanol. The solution was heated at reflux for 1 h, followed by cooling to room temperature and concentration in vacuo. The residue was dissolved in 11.5 ml of a 2 M aqueous solution of hydrochloric acid and heated at reflux over night. After cooling the reaction mixture to 0° C. on an ice-water bath were added consecutively 2.8 ml of a 32% aqueous solution of sodium hydroxide and a solution of di-tert-butyl dicarbonate (1.00 g, 4.58 mmol) in 15 ml 1,4-dioxane. The ice-water bath was removed after completed addition and stirring was continued at room temperature for 4 h. The pH of the reaction mixture was adjusted to 8 by the addition of 1 M aqueous sodium hydroxide solution. Washing with two portions of tert-butyl methyl ether was followed by back-extraction of the combined organic layers with 1 M aqueous sodium hydroxide solution. The combined aqueous layers were cooled to 0° C., acidified to pH 1 with ice-cold 4 M aqueous hydrochloric acid solution and extracted with three portions of ethyl acetate. The combined organic layers were washed with brine, dried over sodium sulfate and concentrated in vacuo to give (−)-(3S,4R)-4-(4-fluoro-phenyl)-piperidine-1,3-dicarboxylic acid 1-tert-butyl ester (590 mg, 80%) with 93.8% ee.

MS m/e (%): 322 (M−H$^+$, 100).
[α]$_D$=−0.867 (c=0.462, CHCl$_3$)

d) (3S,4R)-4-(4-Fluoro-phenyl)-3-hydroxymethyl-piperidine-1-carboxylic acid tert-butyl ester

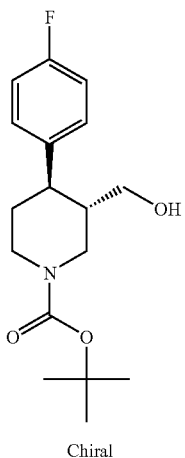

Chiral

To a solution of (−)-(3S,4R)-4-(4-fluoro-phenyl)-piperidine-1,3-dicarboxylic acid 1-tert-butyl ester (1.71 g, 5.29 mmol) in 35 ml THF was added a 2 M borane dimethylsulfide complex solution in THF (5.44 ml, 10.9 mmol) at 0° C. The mixture was stirred for 15 min at 0° C. and then at room temperature over night. After cooling to 0° C. the reaction was quenched by the addition of methanol. Stirring was continued until no evolution of gas was observed any more. The reaction mixture was diluted with water and extracted with 3 portions of tert-butyl methyl ethyl. The combined organic layers were dried over sodium sulfate and concentrated in vacuo. Flash chromatography gave 1.58 g (94%) of the title compound as a colorless viscous oil.

MS m/e (%): 310 (M+H$^+$, 32)

e) (−)-(3S,4R)-3-(3,5-Bis-trifluoromethyl-benzyloxymethyl)-4-(4-fluoro-phenyl)-piperidine-1-carboxylic acid tert-butyl ester

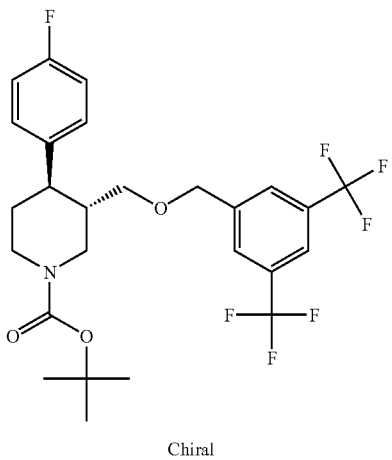

Chiral

To a solution of (3S,4R)-4-(4-fluoro-phenyl)-3-hydroxymethyl-piperidine-1-carboxylic acid tert-butyl ester (1.58 g, 5.11 mmol) in 30 ml DMF were added 0. 29 g (6.0 mmol) sodium hydride (50% in mineral oil) at 0° C. The reaction mixture was allowed to warm to room temperature. After 20 min. 3,5-bis(trifluoromethyl)benzyl bromide (3.14 g, 10.2 mmol) was added. Stirring at room temperature for 2 h was followed by quenching with water and extraction with three portions of tert-butyl methyl ether. The combined organic layers were washed with brine, dried over sodium sulfate and concentrated in vacuo. The crude product was purified by flash column chromatography (silica gel, heptane/ethyl acetate) to give 3.4 g (>100%) of the title compound as a white solid.

MS m/e (%): 536 (M+H$^+$, 13)

[α]$_D$=−5.26 (c=0.362, CHCl$_3$)

f) (−)-(3S,4R)-3-(3,5-Bis-trifluoromethyl-benzyloxymethyl)-4-(4-fluoro-phenyl)-piperidine hydrochloride

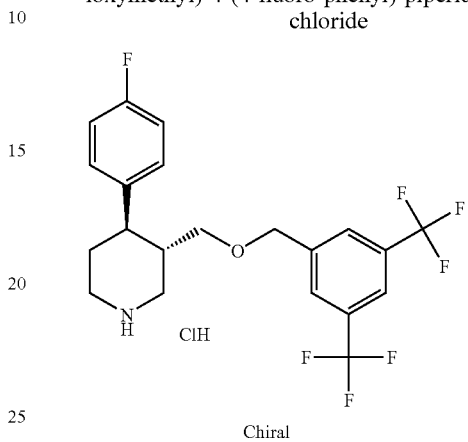

Chiral

A solution of (−)-(3S,4R)-3-(3,5-bis-trifluoromethyl-benzyloxymethyl)-4-(4-fluoro-phenyl)-piperidine-1-carboxylic acid tert-butyl ester (1.10 g, 2.05 mmol) in a 1.25 M solution of hydrochloric acid in methanol (16.4 ml, 3.3 mmol) was stirred for 30 min. at 40° C. The reaction mixture was concentrated to dryness and the residue was partitioned between tert-butyl methyl ether and a 1 M aqueous sodium hydroxide solution. After extraction with three portions of tert-butyl methyl ether the combined organic layers were dried over sodium sulfate and concentrated in vacuo to 0.890 g (99.5%) of the title compound as a colorless white solid.

MS m/e (%): 436 (M+H$^+$, 100)

[α]$_D$=−40.8 (c=0.385, CHCl$_3$)

Example 2

(−)-(3S,4R)-3-(3,5-Bis-trifluoromethyl-benzyloxymethyl)-4-(4-fluoro-phenyl)-piperidine

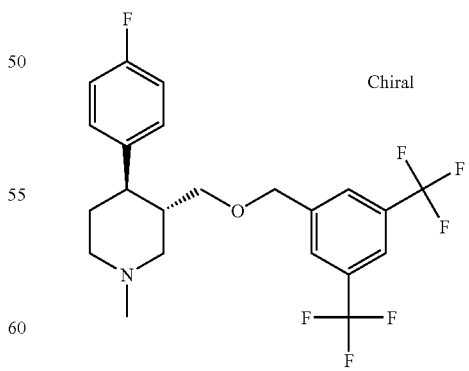

Chiral

A solution of (−)-(3S,4R)-3-(3,5-bis-trifluoromethyl-benzyloxymethyl)-4-(4-fluoro phenyl)-piperidine (121 mg, 0.278 mmol) and paraformaldehyde (67 mg, 2.2 mmol) in 5 ml of methanol was heated at reflux for 2.5 h. The mixture was cooled to 0° C., treated with sodium cyanoborohydride (37 mg, (0.56 mmol) and stirred for 30 min. Quenching with 2 M aqueous hydrochloric acid solution was followed by basification to pH 14 with 2 M aqueous sodium hydroxide solution and extraction with three portions of tert-butyl methyl ether. The combined organic layers were dried over sodium sulfate and concentrated in vacuo. Flash column chromatography gave 85 mg (68%) of the title compound as a colorless amorphous solid.

MS m/e (%): 450 (M+H⁺, 100)
[α]_D=−37.8 (c=0.558, CHCl₃)

Example 3

(−)-[(3S,4R)-3-(3,5-Bis-trifluoromethyl-benzyloxymethyl)-4-(4-fluoro-phenyl)-piperidin-1-yl]-acetonitrile

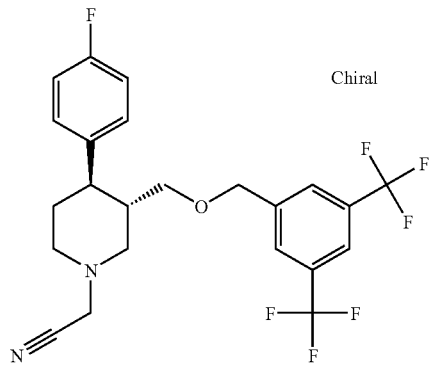

A mixture of (−)-(3S,4R)-3-(3,5-bis-trifluoromethyl-benzyloxymethyl)-4-(4-fluoro-phenyl)-piperidine (150 mg, 0.345 mmol), bromoacetonitrile (45 mg, 0.37 mmol) and potassium carbonate (95 mg, 0.69 mmol) in 4 ml of acetonitrile was stirred at room temperature over night. Quenching with water was followed by extraction with three portions of tert-butyl methyl ether. The combined organic layers were dried over sodium sulfate and concentrated in vacuo. Flash column chromatography gave 163 mg (99.7%) of the title compound as a white solid.

MS m/e (%): 475 (M+H⁺, 100)
[α]_D=−46.16 (c=0.496, CHCl₃)

Example 4

(−)-(3S,4R)-4-(4-Fluoro-phenyl)-3-(3-trifluoromethyl-benzyloxymethyl)-piperidine hydrochloride

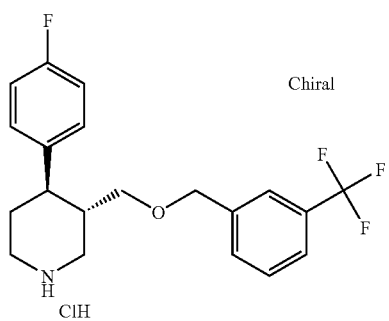

The title compound was obtained as a light yellow amorphous solid in comparable yields according to steps e) and f) of the procedure described above for the preparation of (−)-(3S,4R)-3-(3,5-bis-trifluoromethyl-benzyloxymethyl)-4-(4-fluoro-phenyl)-piperidine hydrochloride using 3-trifluoromethylbenzyl bromide instead of 3,5-bis(trifluoromethyl) benzyl bromide in step e).

MS m/e (%): 368 (M+H⁺, 100)
[α]_D=−39.93 (c=0.431, CHCl₃)

Example 5

(3SR,4RS)-3-(3,5-Bis-trifluoromethyl-benzyloxymethyl)-4-phenyl-piperidine hydrochloride

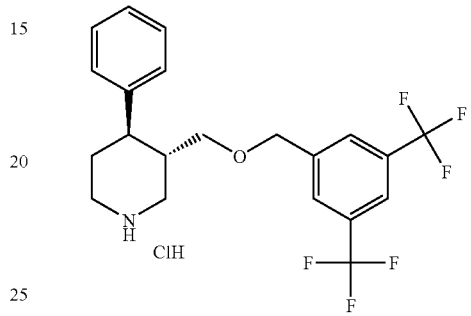

The title compound was obtained as a light yellow amorphous solid in comparable yields according to the procedure described above for the preparation of (−)-(3S,4R)-3-(3,5-bis-trifluoromethyl-benzyloxymethyl)-4-(4-fluoro-phenyl)-piperidine hydrochloride using (3SR,4RS)-4-(phenyl)-piperidine-1,3-dicarboxylic acid 1-tert-butyl ester instead of (−)-(3S,4R)-4-(4-fluoro-phenyl)-piperidine-1,3-dicarboxylic acid 1-tert-butyl ester in step d).

MS m/e (%): 418 (M+H⁺, 100)

Example 6

(−)-(trans)-3-(3,5-Bis-trifluoromethyl-benzyloxymethyl)-4-o-tolyl-piperidine hydrochloride a) (+)-(cis)-4-o-Tolyl-piperidine-1,3-dicarboxylic acid 1-tert-butyl ester

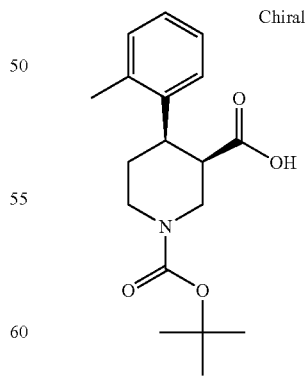

The title compound was obtained as white crystals in 98.1% ee after crystallization from n-heptane/ethyl acetate according to the procedure described above for the preparation of (+)-(3R,4R)-4-(4-fluoro-phenyl)-piperidine-1,3-dicarboxylic acid-1-tert-butyl ester described above using Ru(OAc)2((S)-BITIANP) instead of [Ru(OAc)$_2$((S)-3,5-Xyl-4-MeO)-MeOBIPHEP].

MS m/e (%): 318 (M−H$^+$, 100)
[α]$_D$=+78.71 (c=0.700, CHCl$_3$)

HPLC Method for ee Determination:
Chiralpak-ADH column, 25 cm*4.6 mm, 85% n-heptane+ 15% ethanol with 1% trifluroacetic acid, flow 0.7 ml/min, 20° C., 0.005 ml injection volume, 215 nm. Retention times: (−)-acid 8.1 min, (+)-acid 8.8 min.

b) (−)-(trans)-3-(3,5-Bis-trifluoromethyl-benzyloxymethyl)-4-o-tolyl-piperidine hydrochloride

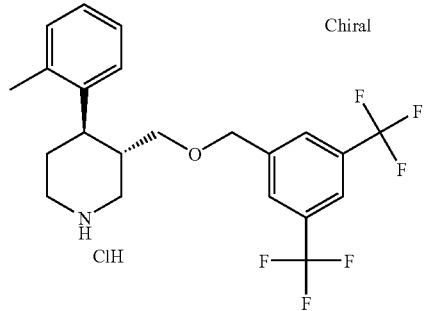

The title compound was obtained as a colorless amorphous solid in comparable yields according to steps b) to f) of the procedure described above for the preparation of (−)-(3S,4R)-3-(3,5-bis-trifluoromethyl-benzyloxymethyl)-4-(4-fluoro-phenyl)-piperidine hydrochloride using (+)-(cis)-4-o-tolyl-piperidine-1,3-dicarboxylic acid 1-tert-butyl ester instead of (+)-(3R,4R)-4-(4-fluoro-phenyl)-piperidine-1,3-dicarboxylic acid-1-tert-butyl ester in step b).

MS m/e (%): 432 (M+H$^+$, 100)
[α]$_D$=−33.36 (c=0.408, CHCl$_3$)

Example 7

5-(3,5-Bis-trifluoromethyl-benzyloxymethyl)-4-o-tolyl-1,2,3,6-tetrahydro-pyridine hydrochloride a) 1-Benzyl-3-(3,5-bis-trifluoromethyl-benzyloxymethyl)-4-o-tolyl-pyridinium bromide

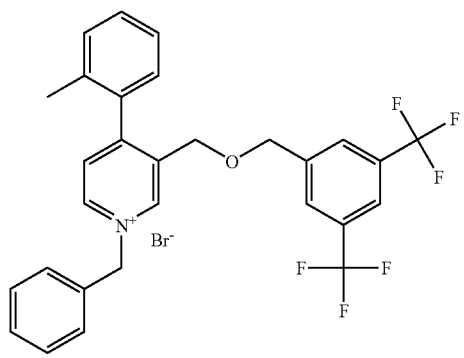

To a solution of 3-(3,5-bis-trifluoromethyl-benzyloxymethyl-4-o-tolyl-pyridine (prepared as described in DE 10008042 A1; 150 mg, 0.353 mmol) and benzyl bromide (60 mg, 0.35 mmol) in 3 ml acetonitrile was heated at reflux for 5 h. The mixture was concentrated in vacuo and the residue was purified by flash column chromatography to give 163 mg (78%) of the title compound as a white solid.

MS m/e (%): 516 (M$^+$, 100).

b) 1-Benzyl-5-(3,5-bis-trifluoromethyl-benzyloxymethyl)-4-o-tolyl-1,2,3,6-tetrahydro-pyridine

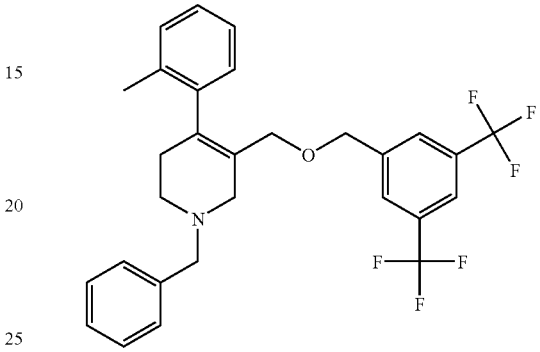

A solution of 1-benzyl-3-(3,5-bis-trifluoromethyl-benzyloxymethyl)-4-o-tolyl-pyridinium bromide (163 mg, 0.273 mmol) in 6 ml of ethanol was added sodium borohydride (10 mg, 0.26 mmol) at 0° C. The mixture was heated to 35° C. and stirred at this temperature over night. Another portion of sodium borohydride (10 mg, 0.26 mmol) was added and the mixture was heated to 50° C. for 2 h. After cooling to room temperature and quenching with water the mixture was diluted with a saturated aqueous solution of sodium carbonated and extracted with three portions of tert-butyl methyl ether. The combined organic layers were dried over sodium sulfate and concentrated in vacuo. Flash column chromatography gave 78 mg (55%) of the title compound as a light yellow oil.

MS m/e (%): 520 (M+H$^+$, 100).

c) 5-(3,5-Bis-trifluoromethyl-benzyloxymethyl)-4-o-tolyl-1,2,3,6-tetrahydro-pyridine hydrochloride

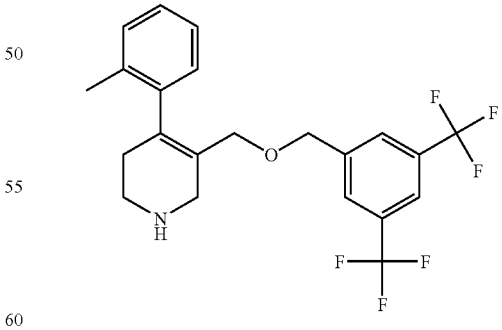

A mixture of 1-benzyl-5-(3,5-bis-trifluoromethyl-benzyloxymethyl)-4-o-tolyl-1,2,3,6-tetrahydro-pyridine (76 mg, 0.15 mmol), potassium carbonate (20 mg, 0.15 mmol) and 1-chloroethyl chloroformate (23 mg, 0.16 mmol) in 3 ml of 1,2-dichloroethane was heated at 50° C. for 3 h. The mixture was filtered and concentrated in vacuo. The residue was dissolved in 2 ml of methanol and heated at reflux over night. Evaporation of the solvent in vacuo was followed by flash column chromatography to give the free base of the title compound. Dissolution in a 2 M solution of hydrochloric acid in diethyl ether and concentration in vacuo gave 57 mg (84%) of the title compound as a white solid.

MS m/e (%): 430 (M+H$^+$, 100)

The invention claimed is:

1. A compound of formula I-A

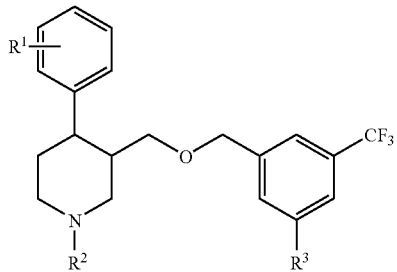

I-A wherein
R$^1$ is hydrogen, halogen or lower alkyl;
R$^2$ is —(CH$_2$)$_n$CN;
R$^3$ is hydrogen or CF$_3$; and
n is 1 or 2;
or a pharmaceutically acceptable acid addition salt thereof.

2. A compound of claim 1, which is (−)-(3S,4R)-3-(3,5-bis-trifluoromethyl-benzyloxymethyl)-4-(4-fluoro-phenyl)-piperidine.

3. A compound of formula I-B

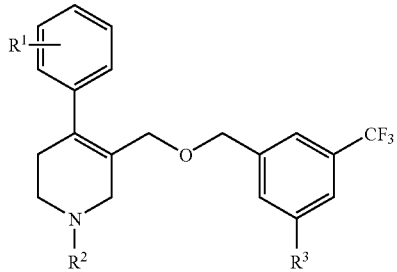

I-B wherein
R$^1$ is hydrogen, halogen or lower alkyl;
R$^2$ is hydrogen, lower alkyl or —(CH$_2$)$_n$CN;
R$^3$ is hydrogen or CF$_3$; and
n is 1 or 2;
or a pharmaceutically acceptable acid addition salt thereof.

4. A compound of claim 3, which is 5-(3,5-bis-trifluoromethyl-benzyloxymethyl)-4-o-tolyl-1,2,3,6-tetrahydro-pyridine.

5. A pharmaceutical composition comprising a therapeutically effective amount of a compound of formula I-A

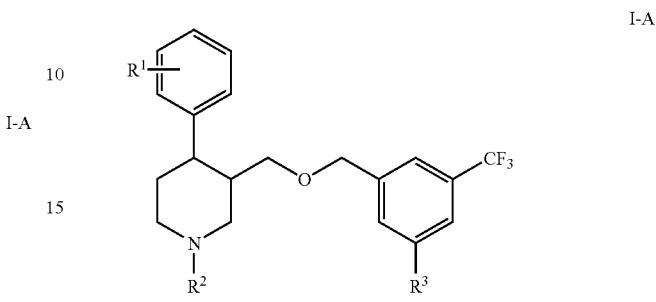

I-A wherein
R$^1$ is hydrogen, halogen or lower alkyl;
R$^2$ is —(CH$_2$)$_n$CN;
R$^3$ is hydrogen or CF$_3$; and
n is 1 or 2;
or a pharmaceutically acceptable acid addition salt thereof and a pharmaceutically acceptable carrier.

6. A pharmaceutical composition comprising a therapeutically effective amount of a compound of formula I-B

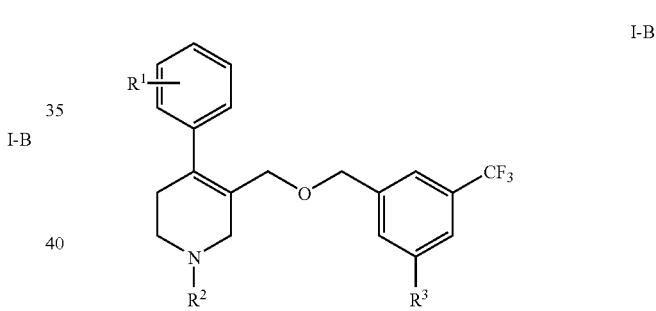

I-B wherein
R$^1$ is hydrogen, halogen or lower alkyl;
R$^2$ is hydrogen, lower alkyl or —(CH$_2$)$_n$CN;
R$^3$ is hydrogen or CF$_3$; and
n is 1 or 2;
or a pharmaceutically acceptable acid addition salt thereof and a pharmaceutically acceptable carrier.

* * * * *